(12) United States Patent
Chang et al.

(10) Patent No.: US 9,474,775 B2
(45) Date of Patent: Oct. 25, 2016

(54) COMPOUND, EXTRACT ISOLATED FROM ANTRODIA CAMPHORATE, AND METHOD USING THE SAME

(71) Applicant: Hui Ling Tseng, Taipei (TW)

(72) Inventors: Wen-Liang Chang, New Taipei (TW); Chen-Wen Yao, Taipei (TW); I-Chuan Yen, Taipei (TW); Hui Ling Tseng, Taipei (TW); Wan Ping Tseng, Taipei (TW); Tai Lin Tseng, Taipei (TW); Yin Yu Kuo, Taipei (TW)

(73) Assignee: Hui Ling Tseng, Taipei (TW)

( * ) Notice: Subject to any disclaimer, the term of this patent is extended or adjusted under 35 U.S.C. 154(b) by 486 days.

(21) Appl. No.: 13/960,764

(22) Filed: Aug. 6, 2013

(65) Prior Publication Data

US 2014/0335122 A1    Nov. 13, 2014

(30) Foreign Application Priority Data

May 9, 2013   (TW) .............................. 102116537 A

(51) Int. Cl.
| | | |
|---|---|---|
| *A61K 36/07* | (2006.01) | |
| *A61K 31/12* | (2006.01) | |
| *A61K 31/122* | (2006.01) | |
| *C07C 403/08* | (2006.01) | |

(52) U.S. Cl.
CPC ............. *A61K 36/07* (2013.01); *A61K 31/122* (2013.01); *C07C 403/08* (2013.01); *A61K 2236/00* (2013.01); *C07C 2101/16* (2013.01)

(58) Field of Classification Search
None
See application file for complete search history.

(56) References Cited

PUBLICATIONS

Cherng, I. H., and Chiang, H. C. 1995. Three new triterpenoids from Antrodia cinnamomea. J. Nat. Prod. 58:365-371.
Chen, C. H., and Yang, S. W. 1995. New steroid acids from Antrodia cinnamomea,—a fungus parasitic on Cinnamomum micranthum. J. Nat. Prod. 58:1655-1661.
Chiang, H. C., Wu, D. P., Cherng, I. W., and Ueng, C. H. 1995. A sesquiterpene lactone, phenyl and biphenyl compounds from Antrodia cinnamomea. Phytochemistry. 39:613-616.
Cherng, I. H., Wu, D. P., and Chiang, H. C. 1996. Triterpenoids from Antrodia cinnamomea. Phytochemistry. 41:263-267.
Yang, S. W., Shen, Y. C., and Chen, C. H. 1996. Steroids and triterpenoids of Antrodia cinnamomea—a fungus parasitic on Cinnamomum micranthum. Phytochemistry. 41:1389-1392.

*Primary Examiner* — Chris R Tate
*Assistant Examiner* — Randall Winston
(74) *Attorney, Agent, or Firm* — WPAT, P.C., Intellectual Property Attorneys; Anthony King

(57) ABSTRACT

Disclosed is a compound isolated from *Antrodia camphorata*, represented by formula I:

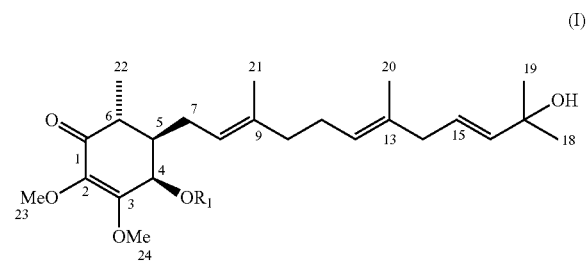

wherein R1 is a hydrogen atom or an acetyl group; and a method of inhibiting cancer cell growth by using the compound, the cancer is selected from the group consisting of lung cancer, colon cancer, prostate cancer, liver cancer and breast cancer.

1 Claim, No Drawings

COMPOUND, EXTRACT ISOLATED FROM ANTRODIA CAMPHORATE, AND METHOD USING THE SAME

CROSS-REFERENCES TO RELATED APPLICATIONS

This application claims the priority of Taiwanese patent application No. 102116537, filed on May 9, 2013, which is incorporated herewith by reference.

BACKGROUND OF THE INVENTION

1. Field of the Invention

The present invention relates to a compound and extract isolated from *Antrodia camphorata*, particularly relates to a method of inhibiting cancer cell growth by using the compound.

2. The Prior Arts

*Antrodia camphorata* is also called Chang-Zhi, Niu Chang-Zhi, red camphor mushroom and the like, which is a perennial mushroom belonging to the order Aphyllophorales, the family Polyporaceae. It is an endemic species in Taiwan growing on the inner rotten heart wood wall of *Cinnamomum kanehirae* Hay. *Cinnamoum kanehirai* Hay is rarely distributed and being overcut unlawfully, which makes *Antrodia camphorata* growing inside the tree in the wild became even rare. The price of *Antrodia camphorata* is very expensive due to the extremely slow growth rate of natural *Antrodia camphorata* that only grows between Junes to October.

The fruiting bodies of *Antrodia camphorata* are perennial, sessile, hard and woody, which exhales strong smell of sassafras (camphor aroma). The appearances are various with plate-like, bell-like, hoof-like, or tower-like shapes. They are reddish in color and flat when young, attached to the surface of wood. Then the brims of the front end become little curled tilted and extend to the surroundings. The color turns to be faded red-brown or cream yellow brown, with ostioles all over. This region is of very high medical value.

In traditional Taiwanese medicine, *Antrodia camphorata* is commonly used as an antidotal, liver protective, anticancer drug. *Antrodia camphorata*, like general edible and medicinal mushrooms, is rich in numerous nutrients including polysaccharides (such as β-glucosan), triterpenoids, superoxide dismutase (SOD), adenosine, proteins (immunoglobulins), vitamins (such as vitamin B, nicotinic acid), trace elements (such as calcium, phosphorus and germanium and so on), nucleic acid, agglutinin, amino acids, steroids, lignins and stabilizers for blood pressure (such as antodia acid) and the like. These physiologically active ingredients are believed to exhibit effects such as: anti-tumor activities, increasing immuno-modulating activities, anti-allergy, anti-bacteria, anti-high blood pressure, decreasing blood sugar, decreasing cholesterol and the like.

Triterpenoids are the most studied component among the numerous compositions of *Antrodia camphorata*. Triterpenoids are the summary terms for natural compounds, which contain 30 carbon atoms with the pent acyclic or hex acyclic structures. The bitter taste of *Antrodia camphorata* is from the component of triterpenoids. Three novel ergostane-type triterpenoids (antcin A, antcin B, antcin C) were isolated by Cherng et al. from the fruiting bodies of *Antrodia camphorata* (Cherng, I. H., and Chiang, H. C. 1995. Three new triterpenoids from *Antrodia cinnamomea*. J. Nat. Prod. 58:365-371). Three new compounds zhankuic acid A, zhankuic acid B and zhankuic acid were extracted from the fruiting bodies of *Antrodia camphorata* with ethanol by Chen et al. (Chen, C. H., and Yang, S. W. 1995. New steroid acids from *Antrodia cinnamomea*,—a fungus parasitic on *Cinnamomum micranthum*. J. Nat. Prod. 58:1655-1661). In addition, Cherng et al. also found three other new triterpenoids from the fruiting bodies of *Antrodia camphorata*, which are sesquiterpene lactone and 2 biphenyl derived compounds, 4,7-dimethoxy-5-methyl-1,3-benzodioxole and 2,2',5,5'-teramethoxy-3,4,3',4'-bi-methylenedioxy-6,6'-dimethylbiphenyl (Chiang, H. C., Wu, D. P., Cherng, I. W., and Ueng, C. H. 1995. A sesquiterpene lactone, phenyl and biphenyl compounds from *Antrodia cinnamomea*. Phytochemistry. 39:613-616). In 1996, four novel ergostane-type triterpenoids (antcins E and F and methyl antcinates G and H) were isolated by Cherng et al. with the same analytic methods (Cherng, I. H., Wu, D. P., and Chiang, H. C. 1996. Triteroenoids from *Antrodia cinnamomea*. Phytochemistry. 41:263-267). And two ergostane related steroids, zhankuic acids D and E together with three lanosta related triterpenes, 15 alpha-acetyl-dehydrosulphurenic acid, dehydroeburicoic acid, dehydrosulphurenic acid were isolated by Yang et al. (Yang, S. W., Shen, Y. C., and Chen, C. H.1996. Steroids and triterpenoids of *Antrodia cinnamomea*—a fungus parasitic on *Cinnamomum micranthum*. Phytochemistry. 41:1389-1392). Several compounds were continually found to play important roles for AMPK and TOR signal transduction pathway. Through activating AMPK and inhibiting mTOR translation pathway to reach a well control of G1 phase in tumor cells, and completely block development of tumor cells and cause a series of apoptosis.

SUMMARY OF THE INVENTION

Some extracts of *Antrodia camphorata* were proved to have the foregoing benefits, and their compounds were continually identified. However, for *Antrodia camphorata* extract, whether some compounds with anti-tumor bioactivity or medical use were existed needs further experiments to identify.

An object of the present invention is to provide a compound isolated from *Antrodia camphorata*, represented by formula I:

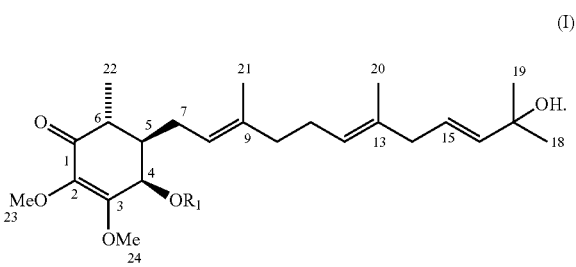

A further object of the present invention is to provide a method of inhibiting cancer cell growth by using the above compounds; the cancer is selected from the group consisting of lung cancer, colon cancer, prostate cancer, liver cancer and breast cancer.

A further object of the present invention is to provide an extract of *Antrodia camphorate* for inhibiting cancer cell growth, extracted by the following steps: extracting a fruiting body, mycelium, or the mixture thereof twice, with an ethanol solution with a ratio of 1:10 to obtain two ethanol extracts, concentrating the ethanol extracts to yield a crude extract, the crude extract being extracted three times with dichloromethane/water (1:1) to form a dichloromethane layer and a water layer, the dichloromethane layer being loaded to a layered silica gel column with hexane/dichloromethane (1:4), dichloromethane, and methanol/dichloromethane (5:95) to yield the extract.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever.

DETAILED DESCRIPTION OF THE PREFERRED EMBODIMENTS

*Antrodia camphorate* Extract

*Antrodia camphorata* fruiting bodies, mycelium or their mixture were provided (1.0 kg) and then extracted twice with an 10-fold ethanol solution to obtain two ethanol extracts. The ethanol extracts were concentrated to yield 230 g crude extract (LE-E). The crude extract was extracted three times with dichloromethane/water (1:1) to form a dichloromethane layer (LT-E-D, 102.6 g) and a water layer (LT-E-W, 127.4 g). Dichloromethane layer (6.0 g) was loaded to a layered silica gel column with hexane/dichloromethane (1:4), dichloromethane, and methanol/dichloromethane (5:95) to yield four layers, respectively ANCA-E-D-1, ANCA-E-D-2, ANCA-E-D-3, and ANCA-E-D-4.

Anti Tumor Activity of *Antrodia camphorata* Extract

Cell proliferation of A549 cell line (lung cancer), CT26 cell line (colon cancer), DU145 cell line (prostate cancer), HepG2 cell line (liver cancer), PC3 cell line (prostate cancer), MDA-MB-231 cell line (breast cancer) and MCF-7 cell line (breast cancer) was assessed by MTT cell viability assay. The results are shown in tables 1~8.

Above cell lines were cultured in determined medium for 24 hours. Proliferative cells were washed with PBS solution, treated with trpsin-EDTA (1×), centrifuged at 1,200 rpm for 5 min, precipitated the cells and discarded supernatant. The cells were resuspended with 10 ml of fresh medium, and then loaded to 96-well plate. While the assay initiated, 0.01~200 μg/ml of *Antrodia camphorata* extract was added in each well, and the plate was incubated for 48 hours, at 37° C., 5% $CO_2$. Each wall was added with 2.5 mg/ml MTT reagent in the dark. After 4 hours of reaction, 100 μl lysis buffer were added to each wall to terminate the reaction. Finally, absorbances were read with an ELISA reader in the wavelength of 570 nm, so as to calculate the cell viability and half maximal inhibitory concentration (IC50). The experiment data was represented by means±SD. All data was statistically analyzed by paired-t test, and a P-value less than 0.05 was considered significant.

TABLE 1

A549 cell line (lung cancer)

| Dose μg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
|---|---|---|---|---|---|---|---|---|---|---|
| 200 | +++ | + | +/− | + | +/− | +/− | +/− | +/− | ++++ | |
| 100 | +++ | + | +/− | + | ++ | +/− | +/− | +/− | ++++ | |
| 50 | +++ | + | ++ | + | ++ | +/− | +++ | +++ | +++ | |
| 25 | +++ | + | ++ | + | ++ | +/− | +++ | ++ | ++++ | |
| 10 | +++ | + | + | ++ | +++ | +/− | + | + | | |
| 1 | +++ | +++ | + | +++ | +++ | + | + | ++ | | |
| 0.1 | +++ | +++ | +++ | +++ | +++ | ++ | + | +++ | | |
| 0.01 | +++ | ++++ | +++ | +++ | ++++ | +++ | +++ | +++ | | 100 |

TABLE 2

CT26 cell line (colon cancer)

| Dose μg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
|---|---|---|---|---|---|---|---|---|---|---|
| 200 | +++ | +/− | +/− | +/− | +/− | +/− | +/− | +/− | +++ | |
| 100 | +++ | +/− | +/− | +/− | + | +/− | +/− | +/− | +++ | |
| 50 | +++ | +/− | +/− | +/− | + | +/− | +/− | + | ++++ | |
| 25 | ++++ | +/− | + | + | + | +/− | + | + | ++++ | |
| 10 | +++ | + | + | ++ | ++ | +/− | + | + | | |
| 1 | ++++ | +++ | + | ++++ | ++++ | +/− | + | + | | |
| 0.1 | ++++ | ++++ | +++ | ++++ | +++ | ++ | + | +++ | | |
| 0.01 | ++++ | +++ | +++ | +++ | +++ | +++ | +++ | +++ | | 100 |

TABLE 3

DU145 cell line (prostate cancer)

| Dose μg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
|---|---|---|---|---|---|---|---|---|---|---|
| 200 | +++ | +/− | +/− | +/− | +/− | +/− | +/− | +/− | +++ | |
| 100 | +++ | +/− | +/− | +/− | + | +/− | +/− | +/− | ++++ | |
| 50 | ++++ | +/− | + | +/− | + | +/− | + | + | +++ | |
| 25 | +++ | +/− | + | +/− | +/− | +/− | + | + | ++++ | |

TABLE 3-continued

DU145 cell line (prostate cancer)

| Dose µg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
|---|---|---|---|---|---|---|---|---|---|---|
| 10 | ++++ | +/− | +/− | +/− | +/− | +/− | +/− | +/− | | |
| 1 | +++ | + | +/− | ++ | +++ | +/− | +/− | +/− | | |
| 0.1 | +++ | +++ | + | +++ | +++ | +/− | +/− | ++ | | |
| 0.01 | +++ | +++ | +++ | +++ | +++ | ++ | ++ | +++ | 100 | |

TABLE 4

HepG2 cell line (liver cancer)

| Dose µg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
|---|---|---|---|---|---|---|---|---|---|---|
| 200 | +++ | +/− | +/− | +/− | +/− | +/− | +/− | +/− | +++ | |
| 100 | +++ | +/− | +/− | +/− | + | +/− | +/− | +/− | +++ | |
| 50 | +++ | +/− | +/− | +/− | + | +/− | +/− | + | ++++ | |
| 25 | +++ | +/− | + | + | ++ | +/− | + | + | ++++ | |
| 10 | +++ | + | + | ++ | +++ | +/− | +/− | + | | |
| 1 | +++ | ++ | + | +++ | ++++ | +/− | + | + | | |
| 0.1 | +++ | +++ | ++ | ++++ | +++ | + | + | +++ | | |
| 0.01 | +++ | +++ | ++ | ++++ | ++++ | ++ | ++ | +++ | 100 | |

TABLE 5

MDCK cell line (kidney from canine)

| Dose µg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
|---|---|---|---|---|---|---|---|---|---|---|
| 200 | +++ | +++ | +/− | ++ | + | +/− | +/− | +/− | +++ | |
| 100 | +++ | +++ | +/− | +++ | ++++ | +/− | +/− | +/− | ++++ | |
| 50 | +++ | +++ | +++ | +++ | +++ | +/− | + | ++ | +++ | |
| 25 | +++ | +++ | +++ | +++ | +++ | + | + | +++ | ++++ | |
| 10 | +++ | +++ | +++ | +++ | +++ | + | +++ | +++ | | |
| 1 | +++ | +++ | +++ | +++ | +++ | + | +++ | ++ | | |
| 0.1 | +++ | +++ | +++ | +++ | +++ | +++ | +++ | +++ | | |
| 0.01 | ++++ | +++ | ++++ | +++ | +++ | ++++ | +++ | ++++ | 100 | |

TABLE 6

PC3 cell line (prostate cancer)

| Dose µg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
|---|---|---|---|---|---|---|---|---|---|---|
| 200 | +++ | +/− | +/− | +/− | +/− | +/− | +/− | +/− | ++++ | |
| 100 | ++++ | +/− | +/− | +/− | + | +/− | +/− | +/− | +++ | |
| 50 | ++++ | +/− | + | +/− | + | +/− | + | + | ++++ | |
| 25 | ++++ | +/− | + | +/− | +/− | +/− | +/− | +/− | +++ | |
| 10 | +++ | +/− | +/− | + | +/− | +/− | +/− | +/− | | |
| 1 | ++++ | + | +/− | +++ | +++ | +/− | +/− | +/− | | |
| 0.1 | ++++ | +++ | + | +++ | +++ | +/− | +/− | +++ | | |
| 0.01 | ++++ | ++++ | +++ | ++++ | ++++ | ++ | ++ | +++ | 100 | |

TABLE 7

MDA-MB-231 cell line (breast cancer)

| Dose µg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
|---|---|---|---|---|---|---|---|---|---|---|
| 100 | ++ | ++ | +/− | + | +/− | +/− | +/− | +/− | +++ | |
| 50 | +++ | + | +/− | + | ++ | +/− | +/− | ++ | +++ | |
| 25 | +++ | + | ++ | ++ | ++ | +/− | ++ | ++ | ++++ | |
| 10 | +++ | ++ | ++ | ++ | ++ | + | ++ | ++ | ++++ | |
| 1 | +++ | ++ | ++ | ++ | +++ | + | + | ++ | | |
| 0.1 | +++ | +++ | +++ | +++ | +++ | ++ | ++ | +++ | | |

TABLE 7-continued

| | | | | | MDA-MB-231 cell line (breast cancer) | | | | | |
|---|---|---|---|---|---|---|---|---|---|---|
| Dose µg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
| 0.01 | +++ | +++ | +++ | +++ | +++ | +++ | +++ | +++ | | |
| 0.001 | +++ | +++ | +++ | +++ | +++ | +++ | +++ | +++ | 100 | |

TABLE 8

| | | | | | MCF-7 cell line (breast cancer) | | | | | |
|---|---|---|---|---|---|---|---|---|---|---|
| Dose µg/ml | DMSO | ANCA-E | ANCA-E-D | ANCA-E-W | ANCA-E-D-1 | ANCA-E-D-2 | ANCA-E-D-3 | ANCA-E-D-4 | 3 days Cell | Blank |
| 100 | ++ | ++ | +/− | ++ | +++ | +/− | +/− | +/− | ++++ | |
| 50 | ++ | ++ | ++++ | ++ | +++ | +/− | ++++ | ++++ | ++++ | |
| 25 | +++ | ++ | +++ | ++ | ++ | +++ | ++++ | +++ | +++ | |
| 10 | ++++ | + | ++ | ++ | +++ | ++ | +++ | +++ | +++ | |
| 1 | +++ | ++ | ++ | +++ | +++ | + | ++ | ++ | | |
| 0.1 | ++++ | +++ | ++ | +++ | +++ | ++ | ++ | +++ | | |
| 0.01 | ++++ | +++ | +++ | +++ | +++ | +++ | ++ | +++ | | |
| 0.001 | ++++ | ++++ | +++ | ++++ | +++ | +++ | +++ | +++ | 100 | |

The symbols used in tables respectively represent: 0-25% cell viability: +/−; 25~50% cell viability: +; 50~75% cell viability: ++, 75~100% cell viability: +++, >100% cell viability: ++++. The solvent used herein is DMSO, whose IC50 value is 2.34%, which means when the drug is diluted to contain 2.34% of DMSO would cause 50% cell death. In this experiment, when the drug concentration was diluted to 100 µl/ml, DMSO concentration was 0.5%. ANCA-E, ANCA-E-D, ANCA-E-W, ANCA-E-D-1, ANCA-E-D-2, ANCA-E-D-3, and ANCA-E-D-4 are different extracts.

According to the results shown in above tables, ANCA-E-D-2, ANCA-E-D-3, ANCA-E-D-4 can preferably inhibit the survival of various tumor cells. For example, in comparison to the other extracts, ANCA-E-D-2 and ANCA-E-D-3 preferably inhibit survival of A549 cell line (lung cancer), CT26 cell line (colon cancer), DU145 cell line (prostate cancer), HepG2 cell line (liver cancer), MDCK cell line (kidney from canine), PC3 cell line (prostate cancer), MDA-MB-231 cell line (breast cancer) and MCF-7 cell line (breast cancer). Though the effect of ANCA-E-D-4 is lower than ANCA-E-D-2 and ANCA-E-D-3, it still has a moderate inhibition effect thereof. Accordingly, above extracts can be used for treating cancers, such as lung cancer, colon cancer, prostate cancer, liver cancer and breast cancer, and the effective compounds contained in those extracts also can be purified.

Purification of Antrocamol LT3 from *Antrodia camphorate* Extract

According to the above results, ANCA-E-D-3 were subjected to C18 reverse-phase HPLC columns for purification. For ANCA-E-D-3 purification, a fraction collected at 14.5 min (80% MeOH/H$_2$O) was concentrated to yield a novel compound "Antrocamol LT3" (180 mg). The structure of the novel compound was determined as follow.

Antrocamol LT3 was a transparent aqueous product, the molecular formula was determined as: $C_{24}H_{38}O_5$; (4R,5R,6R)-4-hydroxy-5-[(2E,6E,9E)-11-hydroxy-3,7,11-trimethyldodeca-2,6,9-trienyl]-2,3-dimethoxy-6-methylcyclohex-2-enone; molecular weight: 406.

$^1$H-NMR Spectral Data of Antrocamol LT3: $^1$H-NMR (400 MHz, CDCl$_3$): 1.14 (3H, d, J=7.2 Hz,), 1.29 (6H, s), 1.56 (3H, s), 1.63 (3H, s), 1.70 (1H, m), 2.02 (2H), m), 2.08 (2H, t, J=6.4 Hz), 2.21 (2H, t, J=7.6 Hz), 2.51 (1H, dq, J=11.2, 7.2 Hz), 2.64 (1H, d, J=5.2 Hz), 3.64 (3H, s), 4.05 (3H, s), 4.32 (1H, d, J=3.2 Hz), 5.08 (1H, t, J=6.8 Hz), 5.14 (1H, t, J=6.4 Hz), 5.57 (2H, m); $^{13}$C-NMR (100 MHz, CDCl$_3$): 12.32 (q), 16.14 (q), 16.14 (q), 26.35 (t), 26.95 (t), 29.85 (q), 39.63 (t), 40.24 (d), 42.20 (t), 43.40 (d), 59.29 (q), 60.59 (q), 67.88 (d), 70.76 (d), 121.14 (d), 124.78 (d), 125.22 (d), 134.04 (s), 135.84 (s), 137.77 (s), 139.17 (d), 160.59 (s), 197.21 (s)

TABLE 9

| | CT26 µg/ml | A549 µg/ml | HepG2 µg/ml | PC3 µg/ml | DU-145 µg/ml | MDA-MB-231 µg/ml | MCF-7 µg/ml |
|---|---|---|---|---|---|---|---|
| ANCA-E | 10 | 10 | 10 | 1 | 1 | 20.28 ± 1.21 | >100 |
| ANCA-E-D | 1 | 1 | 1 | 0.1 | 0.1 | 30.72 ± 0.97 | 35.03 ± 4.32 |
| ANCA-E-D-3 | 0.1 | 0.1 | 0.1 | 0.1 | 0.1 | 26.53 ± 1.82 | 30.85 ± 1.19 |
| Antrocamol LT3 | 0.011 ± 0.001 | 0.014 ± 0.002 | 0.004 ± 0.001 | 0.009 ± 0.001 | 0.070 ± 0.001 | 1.01 ± 0.06 | 0.10 ± 0.01 |

The half maximal inhibitory concentration (IC50) is a measure of the effectiveness of a compound in inhibiting biological or biochemical function. This quantitative measure indicates how much of a particular drug or other substance (inhibitor) is needed to inhibit a given biological process (e.g. cell apoptosis-inducing activity of a compound) by half. As shown in table 9, novel compounds Antrocamol LT3, and extracts of ANCA-E, ANCA-E-D and ANCA-E-D-3 had a predominant anti cancer activity for various cancers, such as lung cancer, colon cancer, prostate cancer, liver cancer and breast cancer. In the future, based on the present invention, these novel compounds and extracts can be further developed to anti cancer drugs.

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of inhibiting cancer cell growth comprising administering an effective amount of a compound isolated from *Antrodia camphorate*, represented by formula I, to a subject in need thereof,

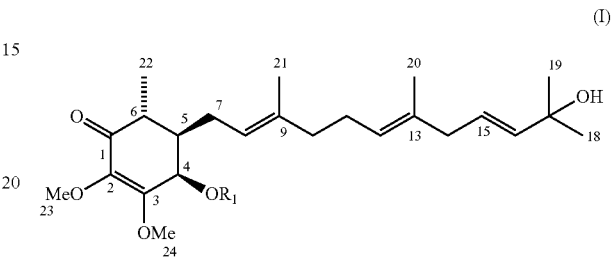

wherein R1 is a hydrogen atom or an acetyl group; and wherein the cancer is selected from the group consisting of lung cancer, colon cancer, prostate cancer, liver cancer and breast cancer.

* * * * *